(12) United States Patent
Seedhom et al.

(10) Patent No.: US 7,632,311 B2
(45) Date of Patent: Dec. 15, 2009

(54) REPAIR OF DAMAGED TISSUE ON A BONE SITE

(75) Inventors: Bahaa Botros Seedhom, Leeds (GB); Jonathan Charles Lorrison, Leeds (GB)

(73) Assignee: Xiros PLC, Leeds (GB)

( * ) Notice: Subject to any disclaimer, the term of this patent is extended or adjusted under 35 U.S.C. 154(b) by 123 days.

(21) Appl. No.: 10/577,886

(22) PCT Filed: Oct. 27, 2004

(86) PCT No.: PCT/GB2004/004536

§ 371 (c)(1), (2), (4) Date: Apr. 28, 2006

(87) PCT Pub. No.: WO2005/051242

PCT Pub. Date: Jun. 9, 2005

(65) Prior Publication Data

US 2007/0073394 A1 Mar. 29, 2007

(30) Foreign Application Priority Data

Oct. 28, 2003 (GB) ................................ 0325141.0

(51) Int. Cl.
*A61F 2/28* (2006.01)
*A61F 2/08* (2006.01)
(52) U.S. Cl. ................. 623/16.11; 623/14.12; 606/300
(58) Field of Classification Search ............ 623/14.12, 623/13.12, 13.11, 23.72, 16.11; 606/60
See application file for complete search history.

(56) References Cited

U.S. PATENT DOCUMENTS 5,207,712 A * 5/1993 Cohen ..................... 623/21.19
5,921,986 A * 7/1999 Bonutti ..................... 606/60
5,989,269 A * 11/1999 Vibe-Hansen et al. ....... 606/151

(Continued)

FOREIGN PATENT DOCUMENTS

DE 20303205 U1 4/2003

(Continued)

*Primary Examiner*—Eduardo C Robert
*Assistant Examiner*—Jason-Dennis Stewart
(74) *Attorney, Agent, or Firm*—Kirton & McConkie; Evan R. Witt

(57) ABSTRACT

A repair kit for use in the repair of damaged cartilage present at or on the surface of a bone site in an animal or human, in which the damaged cartilage is removed from the site and a groove is formed about the site and into the bone prior to implantation of the repair kit. The repair kit includes: a pad of bio-compatible material shaped and dimensioned to occupy at least part of the site from which the damaged tissue has been removed. Elongate connecting portions are attached to the periphery of the pad in an array corresponding in shape to the groove. The connecting portions extend away from the general plane of the pad so as to be introduced into the groove and to be anchored therein. A retaining element is slidable depthwise of the groove to anchor at least some of the connecting portions in the groove and thereby locate and retain the pad in the part of the bone site. There is also disclosed a method of preparation of the bone site prior to implantation, and also an implant delivery device, on which the repair kit can be temporarily stored, and which also serves to deliver the pad, the elongate connecting portions and the retaining element on to the prepared site.

16 Claims, 12 Drawing Sheets

U.S. PATENT DOCUMENTS

| | | | |
|---|---|---|---|
| 6,045,551 A * | 4/2000 | Bonutti | 606/60 |
| 6,080,194 A | 6/2000 | Pachence et al. | |
| 6,117,160 A * | 9/2000 | Bonutti | 606/215 |
| 6,283,980 B1 * | 9/2001 | Vibe-Hansen et al. | 606/151 |
| 6,379,367 B1 * | 4/2002 | Vibe-Hansen et al. | 606/151 |
| 6,468,314 B2 * | 10/2002 | Schwartz et al. | 623/23.72 |
| 6,638,279 B2 * | 10/2003 | Bonutti | 606/60 |
| 6,858,042 B2 * | 2/2005 | Nadler et al. | 623/11.11 |
| 7,163,563 B2 * | 1/2007 | Schwartz et al. | 623/23.76 |
| 7,264,634 B2 * | 9/2007 | Schmieding | 623/14.12 |
| 2002/0010513 A1 * | 1/2002 | Schmieding | 623/23.72 |
| 2002/0042624 A1 * | 4/2002 | Johanson et al. | 606/179 |
| 2002/0151975 A1 * | 10/2002 | Farr et al. | 623/14.12 |
| 2003/0036801 A1 | 2/2003 | Schwartz et al. | |
| 2007/0005138 A9 * | 1/2007 | Goulet et al. | 623/13.17 |
| 2007/0093896 A1 * | 4/2007 | Malinin | 623/14.12 |

FOREIGN PATENT DOCUMENTS

| | | |
|---|---|---|
| DE | 10162205 A1 | 7/2003 |
| WO | 0130276 A | 5/2001 |

* cited by examiner a)

Section A-A:

b)

a)

b)

REPAIR OF DAMAGED TISSUE ON A BONE SITE

This invention relates generally to repair of damaged tissue on a bone site, and which includes bone sites on animals and humans.

The invention has been developed primarily, though not exclusively, in connection with the repair of damaged cartilage and the repair of cartilage defects in synovial human or animal joints, and in particular to provide further improvement in the art over the disclosure in WO01/39694.

BACKGROUND OF THE INVENTION

Reference will be made herein below to the repair of damaged cartilage. It should be understood that the damaged tissue may be other types of tissue including damaged surface bone itself. Reference will also be made herein below to the repair of cartilage of knee joints and again it should be understood that the present invention may be applied to other body joints and indeed to other organs of the body which consist of or incorporate bone.

Defects in the articular surfaces of the knee joint, especially in young active individuals, are currently a focus of interest by orthopaedic surgeons. It is desirable to repair such defects in order to prevent the articular damage from spreading, thereby leading to serious degenerative changes in the joint. Such changes may result in the need for a total knee replacement which is particularly undesirable in young active individuals with a long life expectancy. If the lifetime of the implant is less than that of the patient, a revision procedure may be necessary. Preferably, such revision procedures are to be avoided, having regard to inconvenience to the patient. Furthermore implant revision procedures are both lengthy and very costly. Various techniques for cartilage repair are either in current use or under development but publicly disclosed. The Osteochondral Autogenous Transplant System (OATS) of Arthrex Inc is perhaps the most widely used method. Osteochondral plugs are harvested from a healthy donor and, more particularly, from a site which is claimed to be 'non-weight-bearing'. These plugs are transplanted into the site of the cartilage defect. This procedure has been applied primarily in the knee joint.

However, there are no donor sites in the knee with cartilage of a comparable thickness to that of the deficient site that can be described as 'non-weight-bearing' areas. The solcus terminalis, the most currently used site for harvesting such grafts, is in direct contact with the lateral meniscus at the position of full knee extension, and is therefore a weight-bearing site.

Furthermore, harvesting a large osteochondral plug from the solcus terminalis may cause the lateral meniscus to become lax and impair its load-bearing function. As a result, all the tibio-femoral loads would be transmitted onto the small area of direct contact between the femur and tibia. The resultant stresses could be as high as those arising after meniscectomy with its consequential degenerative changes in the cartilage of the tibial plateau. Such changes have always been regarded as precursors to osteo-arthritis.

While the OATS method provides a reasonable technique, including good instrumentation, for transplanting live autogenous grafts for repair of defects in cartilage, it involves introducing potentially damaging effects at other sites with the serious disadvantages discussed above. In addition, harvesting a plug from a donor site creates a new damage in the knee articular surface. For this reason, OATS would not be suitable for the repair of large defects. The use of OATS for small repairs would probably limit the magnitude of the problem discussed above, but it would also limit the indication for using this technique.

The technique known as Autogenous Chondrocyte Implants (ACI) of Genzyme Inc is a conceptually elegant approach which is gaining popularity. The procedure is intended for repair of small as well as large irregular defects, and is achieved in two stages. In the first stage, chondrocytes (cartilage cells) are harvested from the patient and cultured in suspension. In the second stage of the operative procedure, cartilage residue is cleared from the repair site. The site is then covered with a piece of periosteal tissue which is sutured or glued to the perimeter of the repair area. The chondrocytes are then injected into the repair site using a hypodermic syringe, puncturing the periosteum with the needle of the syringe. In a variation of this procedure, the periosteal tissue is applied to the repair site in the first stage of the operation to ensure that, by the time the chondrocytes are due to be injected, an adequate seal has formed between the tissue and the perimeter of the cartilage. There is a high probability of the chondrocytes escaping through the hole of the hypodermic needle in either version of the procedure.

A further problem with the second version of the procedure is the probability of tissue adhesions occurring between the periosteal tissue and the bottom of the repair site.

This procedure has a low rate of success and the quality of cartilage in the repair site is questionable. As with the OATS method, this procedure is not minimally invasive. It is also a disadvantage that it requires two operative procedures although the first stage is less invasive as it can be performed arthroscopically.

A procedure proposed by Smith & Nephew involves the production of cartilage discs formed by allogeneic chondrocyte culture on an absorbable textile fabric. The discs are grown in the laboratory, the chondrocytes being cultured on a matrix of a non-woven mesh of a bioabsorbable material, typically polyglycolic acid. When this procedure is completed, the disc is supplied for implantation at the repair site.

An advantage of this method is that no damage to an intact healthy chondral site will occur since the method uses allogeneic sources. Furthermore the procedure is completed in a one stage operation.

The discs can be made in different sizes but there must be a limit to the size of the defect which can be repaired with a loose disc which is merely placed in the repair site. The implant could move freely in the joint. It could wrinkle under the influence of tangential forces and, as a result, could be completely damaged. This problem would be exacerbated by the low compressive modulus of the material.

A further disadvantage with this method is that the material, being an allograft, runs the risk of infection. Although a small risk, this is an inherent problem with any allograft.

A further problem to be anticipated with this type of graft is the compressive modulus of the material. It may be quite small and the material might be in need of conditioning to achieve a modulus compatible with that of cartilage of the surrounding area.

The DePuy cartilage repair system is a hexagonal disc of non-woven fabric made of a bioabsorbable material and which has a hard substrate that enables the implant to be attached to the bone. The hexagonal shape of the disc allows repair of damaged areas of irregular shapes by using a plurality of discs in a close-packed array. The disadvantages with this system are that the use of too many adjacent hexagonal discs will result in much damage to the bone substrate, and, further the technique may require considerable skill and its application may also be time consuming.

STATEMENTS OF INVENTION

According to one aspect of the invention there is provided a repair kit for use in the repair of damaged cartilage present at or on the surface of a bone site in an animal or human, in which the damaged cartilage is removed from the site and a groove is formed about the site and into the bone prior to implantation of the repair kit, and said repair kit comprising;

a pad of bio-compatible material shaped and dimensioned to occupy at least part of the site from which the damaged tissue has been removed;

elongate connecting portions attached to the periphery of the pad in an array corresponding in shape to the groove, said portions being intended to extend away from the general plane of the pad so as to be introduced into the groove and to be anchored therein; and a retaining element slidable depthwise of the groove in order to anchor at least some of the connecting portions in the groove and thereby locate and retain the pad in said part of the bone site.

Preferably, the pad is seeded with chondrocytes or cartilage-forming cells prior to implantation.

The elongate connecting portions may be formed by one or more flexible tensile elements taken or "threaded" through the pad, at or near the periphery of the pad, and which can extend generally perpendicular to the plane of the pad so as to be received by the groove with adjacent elements being spaced apart from each other to allow tissue ingrowth to the groove.

A single filament, thread or yarn may be attached to the periphery of the pad, and extend downwardly of the pad in loops of generally parallel lengths.

The retaining element may be pre-attached to the ends of the loops, so that downward movement of the retaining element into the groove pulls the loops downwardly until the pad is received by and then anchored in or at the bone site.

Alternatively, the ends of the loop may first be entered into the groove by other means, including use of an introducer tool, and then the retaining element can be forced downwardly of the groove to engage with the loop ends and pull them downwardly to anchored engagement in the groove.

The retaining element is slidable depthwise of the groove, and may be pre-formed to have a shape corresponding generally with at least part of the shape of the groove, as seen in plan; alternatively, the retaining element may be deformable to take up the required shape, prior to introduction into the groove.

In the case of a circular groove, which is conveniently formed by use of a cylindrical reamer tool, the retaining element will therefore take up the shape of at least part of the circumference of a circle.

In a preferred arrangement, the retaining element comprises a ring, or a near complete ring, and which may be "threaded" through, or connected with, the looped ends of the elongate connecting elements, either during the manufacture of the repair kit, or during the implantation procedures.

The groove can of course take other shapes than circular, including part circular, and the retaining element will correspond in shape to at least part of the shape of the groove. Two or more retaining portions may be provided, to act together in anchoring the looped ends in the groove, but for convenience of implantation it is preferred, wherever possible, that a single retaining element is utilised. Other shapes of pad may include hexagonal or other multi-sided shapes which can interfit with each other to fill the space made available during the preparation of the bone site. One particularly useful shape, for some applications, is a mainly circular shape but having one generally star-shaped or two-sided projection on the periphery of the pad.

Such an arrangement of pad allows a number of similar pads to interfit snugly with each other via interengegement between the respective star shaped teeth. By way of example, with a subtended angle of 120°, three such pads can interfit without leaving any gaps, whereas a subtended angle of 90° will allow four such pads to interfit. This enables the surgeon to build-up a cluster of pads to suit any particular shape of prepared bone site from which damaged cartilage tissue has been removed.

According to a preferred development of the cartilage repair kit of the invention, the implant components (the pad, the elongate connecting portions and the retaining element) are pre-assembled on an implant delivery or implantation device, ready for use by a surgeon when the bone site has been prepared.

The delivery device therefore forms a part of a particularly preferred repair kit according to the invention, and serves a dual purpose of: a) acting as a holder for the assembled implant components of the repair kit during storage and supply from the manufacturer to the customer (and storage by the customer until use); and b) acts as an implant delivery device in order to (i) guide the pad onto the prepared bone site, (ii) introduce the retaining element and the elongate connecting portions into the grooves surrounding the prepared bone site; and (iii) push the retaining element downwardly of the groove to a lower anchor position and thereby to pull the connecting portions downwardly of the groove also and anchor the pad onto the prepared bone site.

The delivery device preferably is hollow, at least at one end thereof, and onto which the retaining element and the pad are fitted ready for presentation by the delivery device to the prepared bone site and the surrounding groove.

The elongate connecting portions may have loose ends which can be arranged on the outer surface of the hollow end of the delivery device, and preferably are retained in position (prior to implantation) by any suitable releasable holding arrangement. In a simple but effective form, the holding arrangement may comprise a band of weak adhesive tape or the like engaging the connecting portions and the outer surface of the hollow end of the delivery device. The holding arrangement may also be a short tubular band that holds the elongate portions in place on the outer side of the delivery device.

When the pad is to be implanted, as the delivery device is introduced in the defect, as it pushes the retaining ring through the groove, the ring drags the elongate connecting portions (threads) downwards into the groove, but the holding arrangement, be it an adhesive tape or short tubular band, is not dragged into the groove but remains at the surface of the defect and retaining its position on the end of the delivery device, so that when the latter is removed from the groove, the said holding arrangement/element is also removed with it.

Preferably, the delivery device is capable of being removably mounted, at its remote end, on a manually operable tool handle. The coupling between the tool handle and the delivery device preferably includes a bearing which permits (unnecessary) turning movement of the tool handle (during manipulation by the surgeon) without transfer of such movement to the delivery device. Therefore, any inadvertent turning of the tool, which may arise in practice during implantation of the repair kit, will not have any adverse effect on the implantation procedure because the delivery device will not itself be rotated.

According to a further aspect of invention, a repair kit as defined above and/or preferred features thereof, may be employed in carrying out a method of repair of damaged cartilage tissue at a bone site of an animal or human being.

According to a third aspect of the present invention there is provided an alternative and improved method of fixation of the general type of device disclosed in WO 01/39694, for the repair of damaged tissue present at or on the surface of bone in an animal, including a human being, the method comprising forming a narrow groove around at least part of said damaged tissue, which groove extends into the bone below the damaged tissue, replacing the tissue around which the groove extends by at least one layer of biocompatible replacement material, and anchoring the material to the bone by the use of retaining means extending from the material into the groove.

Preferably the groove is formed by a reaming device, i.e. a hollow drill.

Preferably the depth of the groove is at least five times that of the thickness of tissue which is replaced. For instance, where the tissue to be replaced is circular, (up to certain limits of diameter), the depth of the groove is preferably at least equal to the diameter of the tissue being replaced.

Preferably the replacement material is in the form of a circular or part circular pad. The material may be bio-absorbable or non-bio-absorbable. It may be seeded with chondrocytes or cartilage-forming cells during surgery.

GENERAL DESCRIPTION OF PREFERRED EMBODIMENTS

The improved device may comprise a pad made of woven or non-woven material, permanent or bioabsorbable when implanted in the body, which is connected to threads made of mono-filamentous- or multi-filamentous yarns, or sutures that are of permanent or bioabsorbable materials when implanted in the body. The threads can be connected to the pad through its substance either parallel to the surfaces of the pad or through the substance of the pad in a substantially perpendicular or inclined direction to the surfaces of the pad (as illustrated in FIG. 1 and FIG. 2), the thread ends (which can be in the form of loops or single ends or both) emerging near the periphery of the pad and projecting from the site where they emerge by a distance of say 30 millimetres (but can be longer or shorter), thus forming means of securing the pad in a narrow groove prepared to surround a repair site prepared as described above. A ring (matching in shape to that of the groove) is fitted into the groove, and which may not necessarily be circular in shape, such ring is made of a biocompatible metal or bioabsorbable material or any other suitable material, and the ring can be made an integral component or made up of segments, said ring being pushed into the groove trapping the treads between both of its surfaces and the two bony surfaces of the groove thus securing the pad in the repair site.

The advantage of the use of threads and retaining rings as per the preferred embodiment, compared with the cover sheet described in the disclosure in WO01/39694 is that the retaining threads do not occupy much space in the annular groove thus allowing bone healing to occur freely within the groove whereas the cover sheet used in the disclosure in WO01/39694 was almost impervious to bone trabeculae that would normally bridge the space across the groove in a normal healing process. Another advantage is that the pad can be substantially of the same diameter as that of the repair site and so the edge of the pad would be in contact with that of the cartilage surrounding the repair site and so expediting the integration of the new tissue with the native cartilage.

In a different configuration the ring and pad and threads can be connected so as to form a unitary device that can perform the same function and be fixed in the repair site in the same manner as described.

Multiple pads can be loosely added below the top pad to stack up to the thickness required for the repair of cartilage in the defective side (as shown in FIG. 3), but in another configuration (as FIG. 4 shows) multiple pads can be connected to the same threads attached to the top pad such that, during surgery, on determining the number of pads required for the repair, some of these pads can be removed leaving the correct number of pads.

Repair sites are preferably delineated with annular grooves of regular shapes that can easily be generated such as circles (as FIG. 5 shows) and so circular pads and circular retaining rings can be used and easily manufactured.

Where repair sites are not possible to encircle with one circular annular groove then the repair can be effected using circular pads and part-circular pads e.g. crescent-shaped pads, the latter being connected to threads in the same manner and retained by portions of rings (as in FIG. 8).

Another example for repair of a larger repair site that may be conveniently enclosed by a larger circle may use two pads, a smaller circular pad and a donut shaped pad that can be placed concentrically in the repair site (as in FIG. 9). The said repair site would have two concentric grooves made, the larger of which would surround and enclose the extent of the defective site. At least two retaining rings would be used to retain the pads using threads attached to the free circular perimeters of the pads as described earlier. The rings can be separate from or connected to their respective pads so that each pad and retaining ring form a unitary device. This principle of lateral stacking of the pads can be extended to repair sites of large areas and complex shapes.

The following describes an instrument for delivery of the implant device just described in this application, i.e. the implant device comprising the pad(s), retaining ring and connecting threads as a unitary device. More detail is now shown in FIG. 10a, concerning a possible configuration of the implant device, and in particular that of the threads connecting the pad to the retaining ring and the geometry of the cross section of the retaining ring. The perspective view of the implant device shows the direction of the connecting threads, which are in two groups perpendicular to each other. The threads are attached to the ring at regularly spaced holes/locating positions. The space on the circumference of the retaining ring between any two adjacent groups of threads is substantially larger than the spacing between any two adjacent points at which the threads are connected to the retaining ring. The vertical view, FIG. 10b, of the implant device is through the plane AA indicated on the perspective view, and shows the cross section of the ring to have a step machined on the inside. This step accommodates the four legs of the delivery device and such legs locate into the retaining ring as shown in FIG. 11. The legs are parts of a cylindrical tube that matches in dimensions those of the retaining ring and extend to just below the lower surface of the pad, but above that level the four legs become joined seamlessly to a cylindrical section that matches in dimensions those of the retaining ring. The pad is attached to other threads that protrude in the opposite direction of the retaining ring and are attached under tension to the cylindrical portion of the delivery instrument. The implant device is thus secured in a stable manner to the delivery instrument with the threads under tension, thus keeping the retaining ring secure within the four legs of the delivery instrument. It is to be noted that, during surgery and prior to implanting the device, if required, additional pads can be passed through the retaining ring and trapped securely under the first pad. The delivery instrument thus loaded with the implant device can simply push the retaining ring and the remainder of the implant device securely in one move into the annular groove surrounding a repair site prepared as described earlier.

Preferred embodiments of the invention will now be described in detail, by way of example only, with reference to the accompanying drawings in which.

Figure 8:
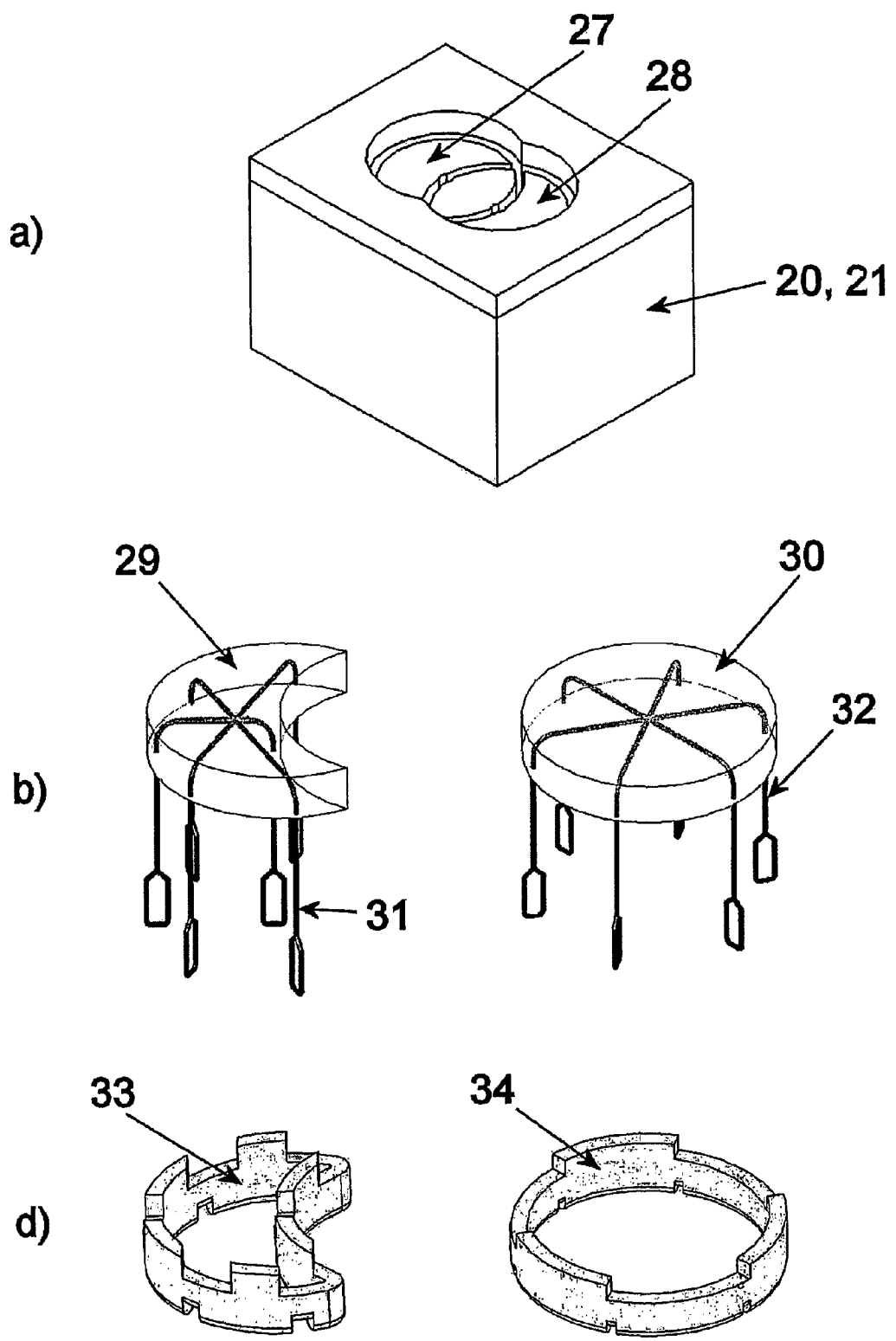
Figure 8:
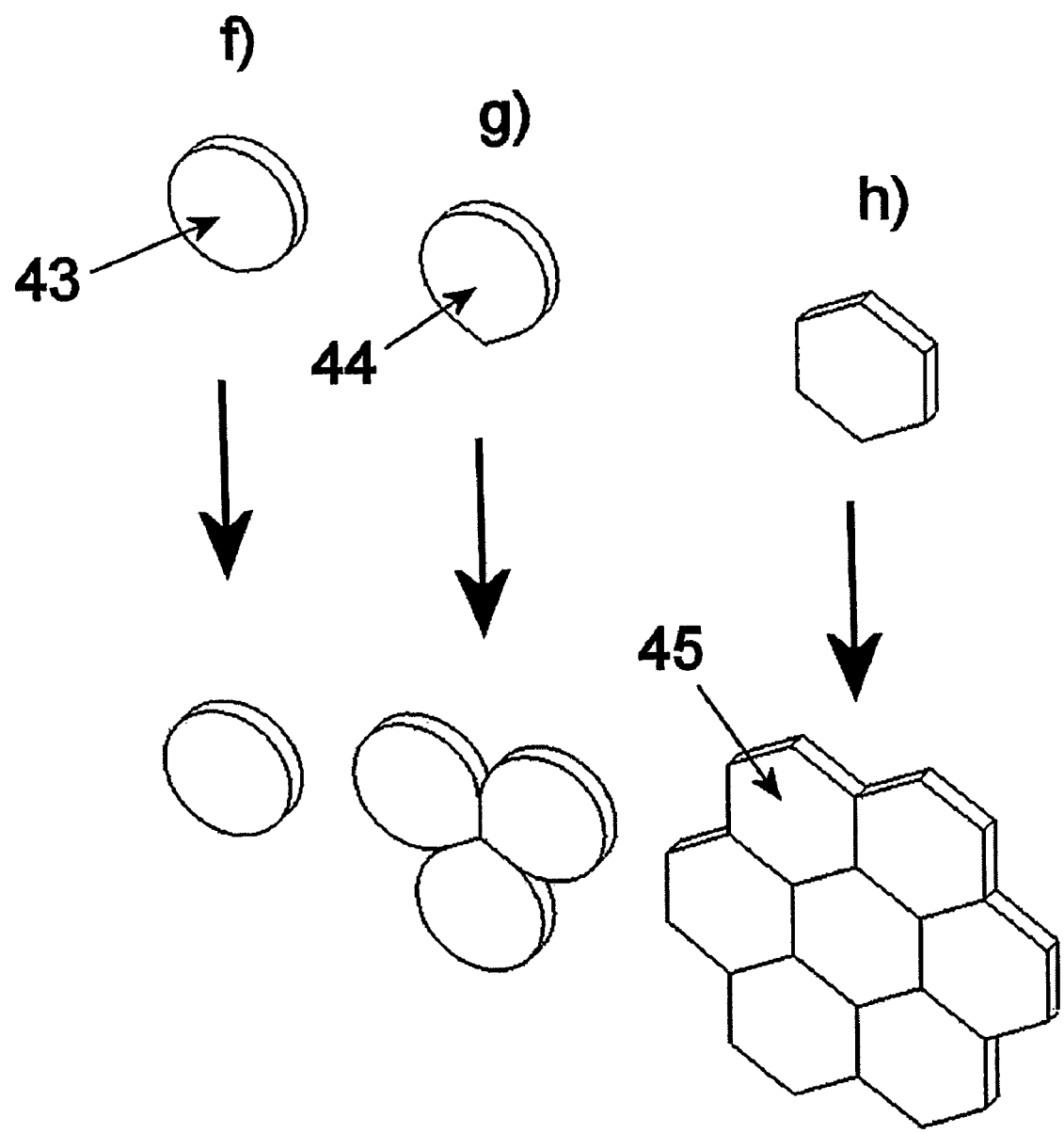
Figure 9:
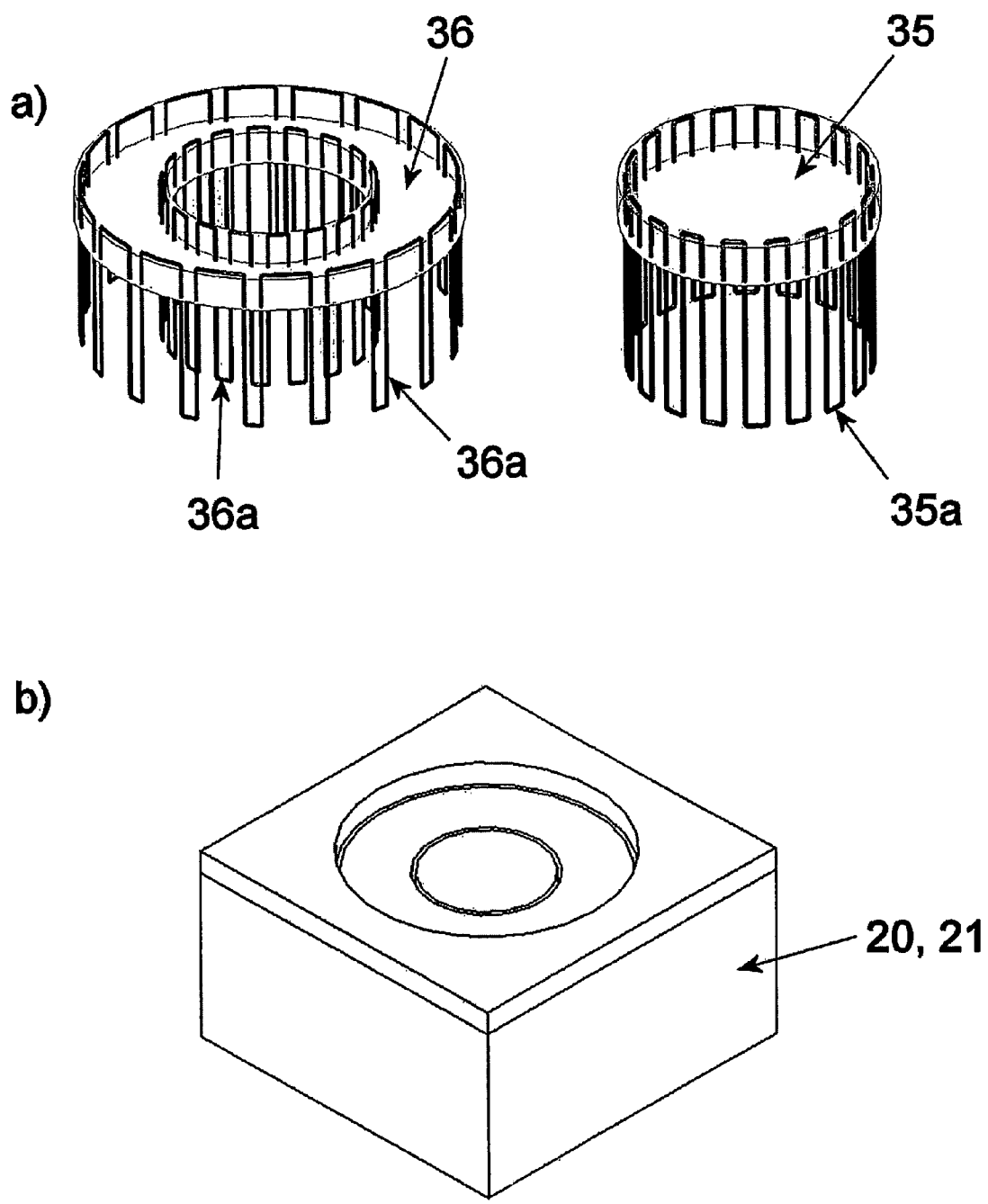
Figure 10:
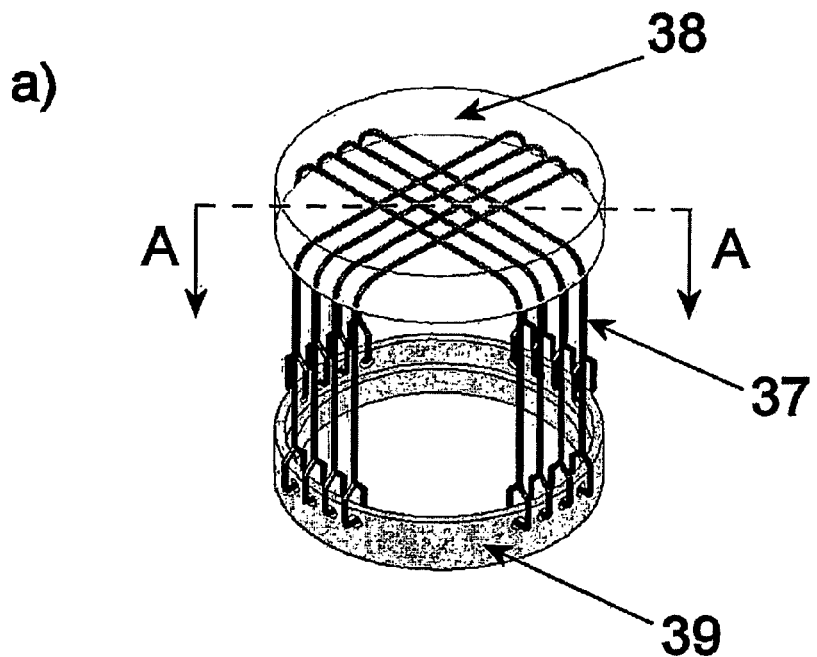
Figure 10:
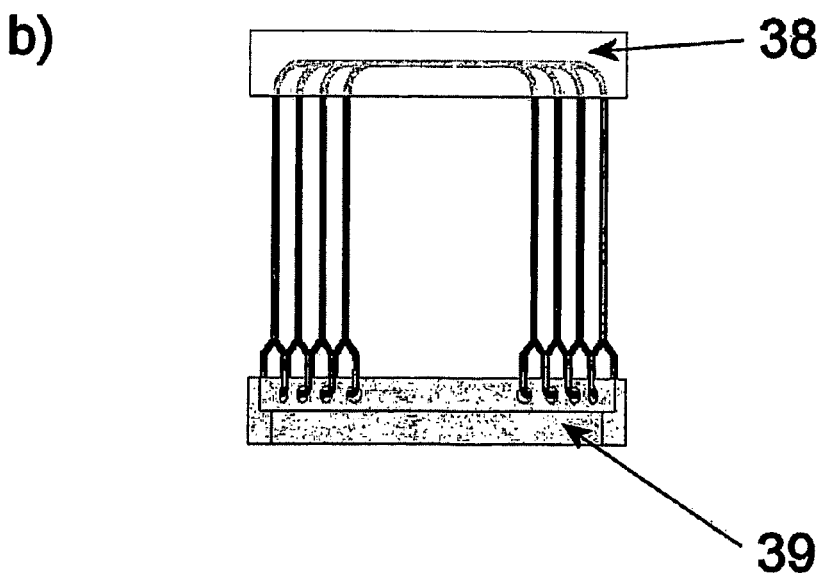

FIGS. 8(a), (b), (c), (d) and (e) show schematically implantation of a repair kit according to the invention on a bone site, in which two separate adjacent portions of damaged tissue are removed, prior to implantation of a pair of co-operating repair kits (having pads of different shape) corresponding to each of the removed portions of damaged tissue material; and FIGS. 8f, g and h show further shapes of pad for use in a repair kit according to the invention;

FIG. 9 illustrates schematically a further example of stacking of pads concentrically for the repair of a lager defect;

FIGS. 10a and 10b are, respectively, a perspective view of a repair kit according to the invention in more detail, and a section on A-A in FIG. 10a;

FIGS. 11a and b are diagrammatic illustrations of an introducer tool for implanting the repair kit disclosed herein.

Figure 12:
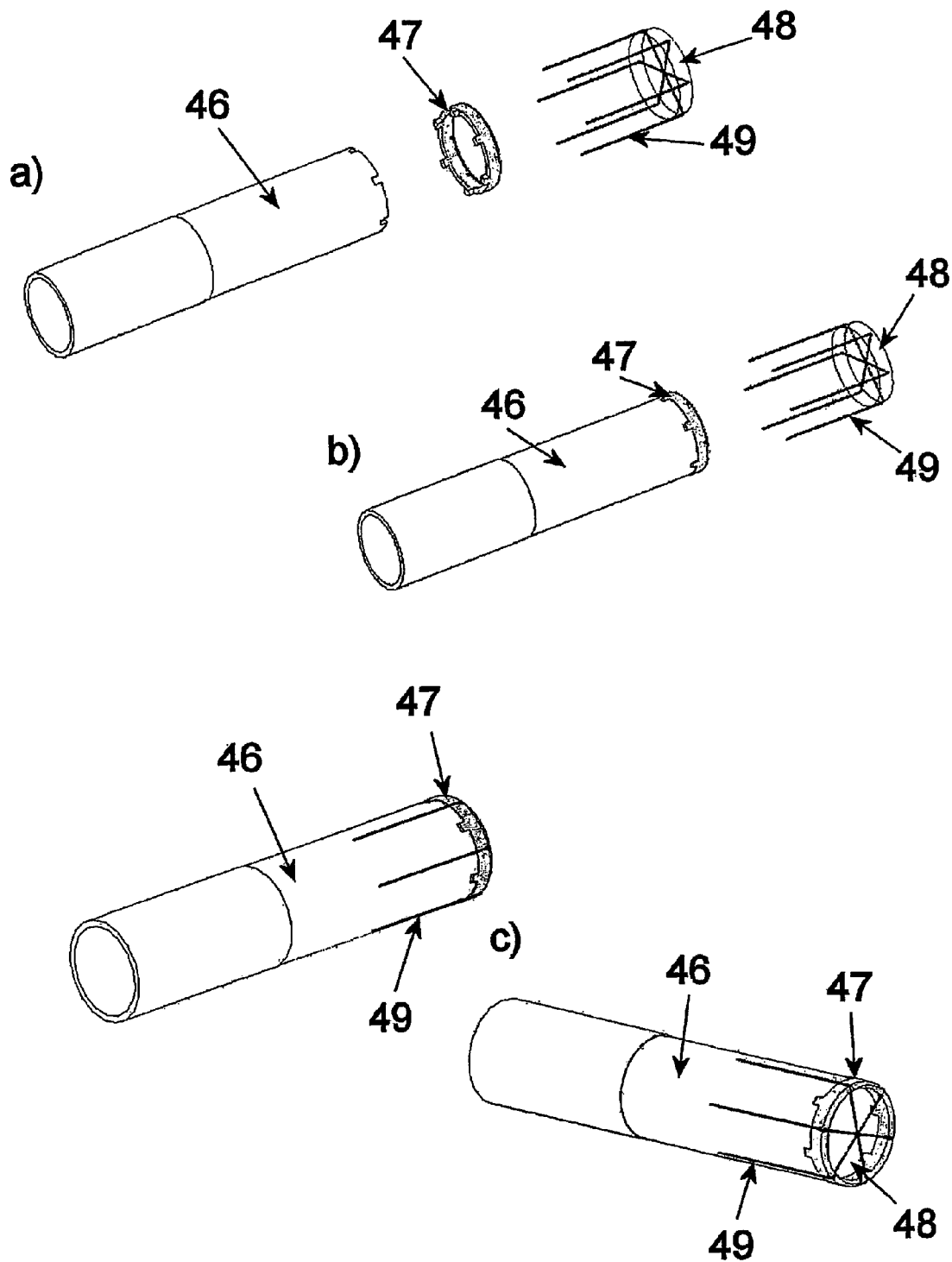
Figure 12:
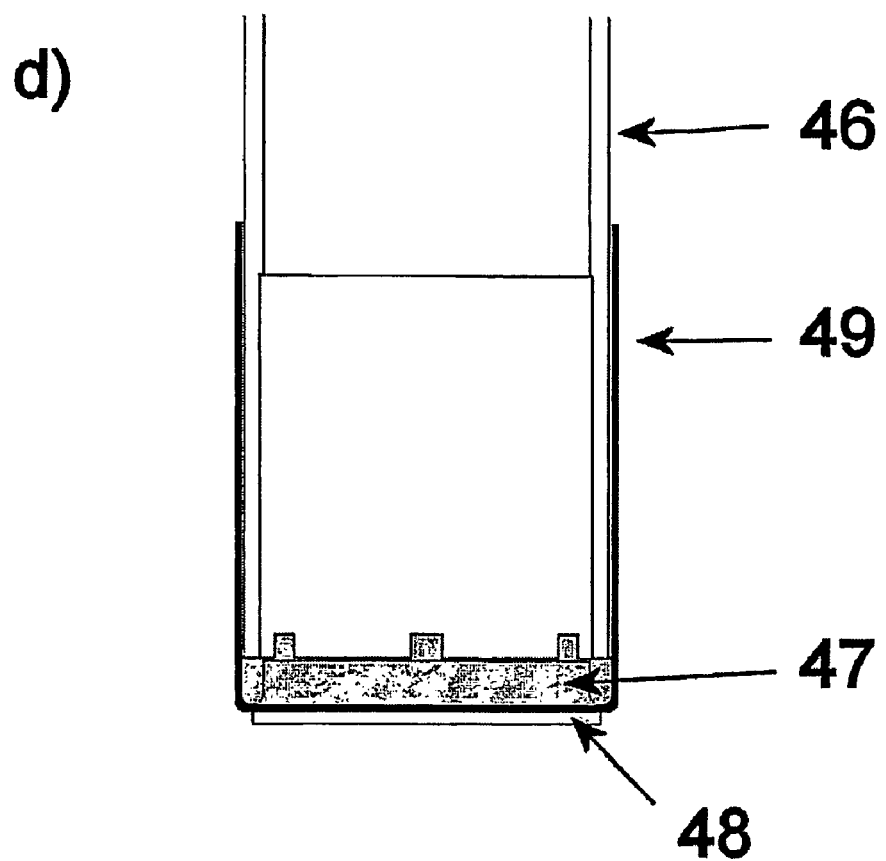

FIGS. 12a to d illustrate successive stageds in the assembly of another embodiment of repair kit according to the invention; and FIGS. 13a to d illustrate, in section or perspective, the approach and entry of the repair kit of FIG. 12 to the prepared bone site.

Figure 1:
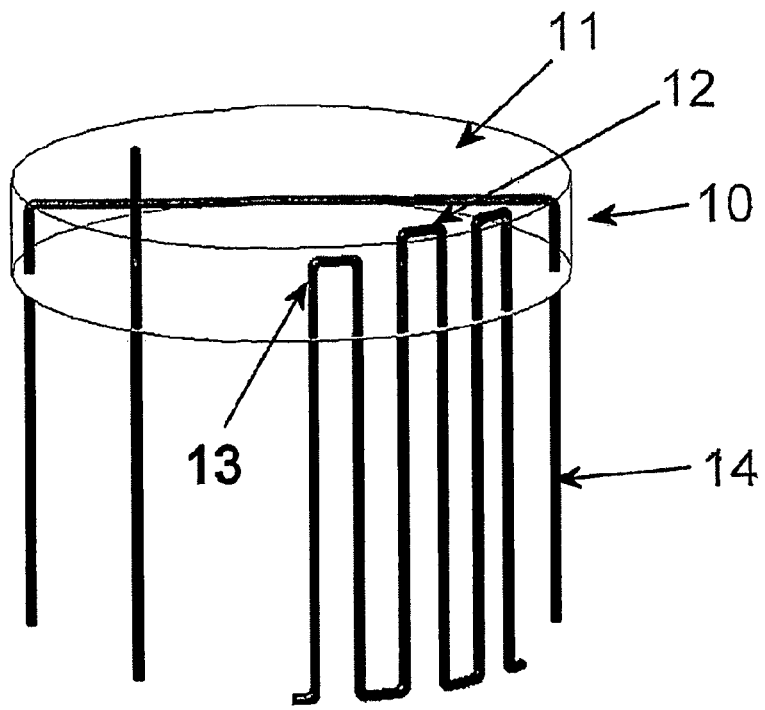
FIG. 1 is a schematic side view illustration of a preferred embodiment of a repair kit according to the invention, for use in carrying out a method of the invention, and which is intended to be used in the repair of damaged tissue such as cartilage present at or on the surface of a bone site in an animal or human being.
Figure 2:
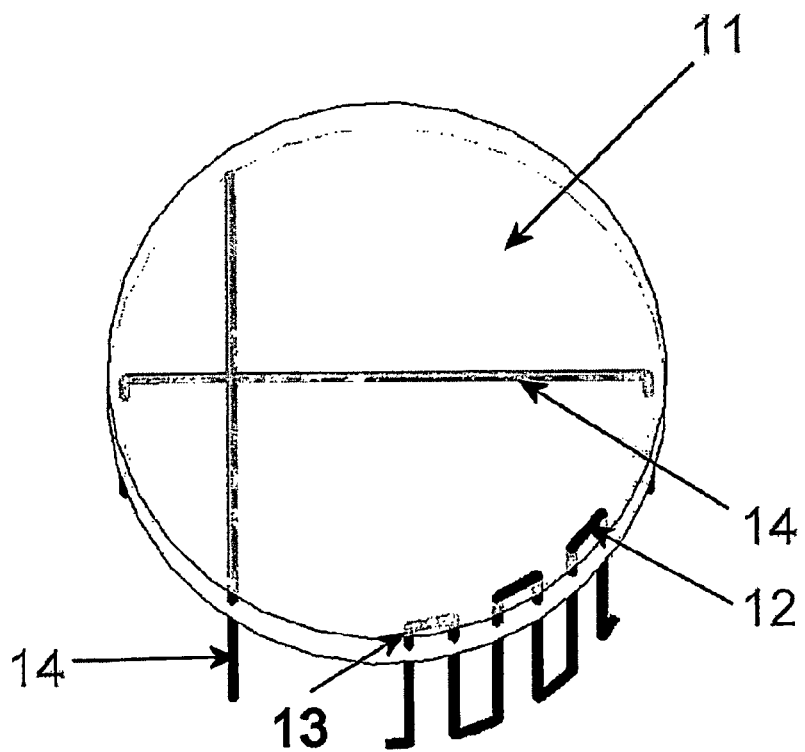
FIG. 2 is a schematic view from above, and in perspective illustration of the repair kit shown in FIG. 1.

Referring first to FIGS. 1 and 2 of the drawings, a repair kit according to the invention is designated generally by reference 10 and is intended to be used in the repair of damaged tissue such as cartilage present at or on the surface of a bone site in an animal or human being. Prior to implantation of the repair kit, the damaged tissue is removed from the site, and a groove is formed about the site and into the bone. The order of removal of the damaged tissue and forming of the groove is not specific and either can be done before the other depending on the instruments that the surgeon might choose to employ during the surgery. This preparation of the bone site ready to receive the repair kit may be carried out, by way of example only, by following these procedures which are described in more detail in international publication No. WO01.39694.

The repair kit 10 comprises a pad 11 of bio-compatible material shaped and dimensioned to occupy at least part of the site from which the damaged tissue has been removed. The kit also includes elongate connecting portions attached to the periphery of pad 11, and forming an array corresponding in shape to the groove, such portions being intended to extend away from the general plane of the pad 11, so as to be introduced into the groove and to be anchored therein.

In the schematically illustrated embodiment of FIGS. 1 and 2, the connecting portions are shown by reference 14, which are loops, or simply loose ends, extending downwardly of the pad 11 in the form of generally parallel lengths which are spaced apart from each other circumferentially of the periphery of the pad. The spacing apart of the generally parallel lengths of connecting portions 14 allows ingrowth of bone tissue to occupy the groove after implantation, and over a period of time. These connecting portions 14, being of small dimensions, will occupy a small space in the groove thus allowing the majority of the groove to be occupied by ingrowth of the bone due to the healing process over a period of time.

The looped connecting portions may be formed by a single filament, thread or length of yarn attached to the periphery of the pad 11, by being "threaded" completely through the pad, as shown at reference 12, or only partially into the body of the pad as shown by reference 13. Connecting portions 14 can also be threaded through the pad in the plane of the pad as indicated in FIG. 2.

To complete the assembly of the repair kit, i.e. to complete the implantation, a retaining element is provided, which is slidable depthwise of the groove in order to anchor at least some of the connecting portions 14 in the groove and thereby locate and retain the pad 11 in the excavated part of the bone site.

The retaining element may be pre-attached to the ends of the loops of the connecting portions 14, so that downward movement of the retaining element into the groove pulls the loops downwardly until the pad 11 is received by and then anchored in or at the bone site.

Alternatively, the ends of the loops may first be entered into the groove by other means, including use of an introducer tool, and then the retaining element can be forced downwardly of the groove to engage with the loop ends and pull them downwardly to anchored engagement in the groove.

The retaining element is slidable depthwise of the groove, and may be pre-formed to have a shape corresponding generally with at least part of the shape of the groove, as seen in plan. Alternatively, the retaining element may be deformable to take up the required shape, prior to introduction into the groove.

In the case of a circular groove, which is conveniently formed by use of a cylindrical reamer tool, the retaining element will therefore take up the shape of least part of the circumference of a circle.

Figure 3:
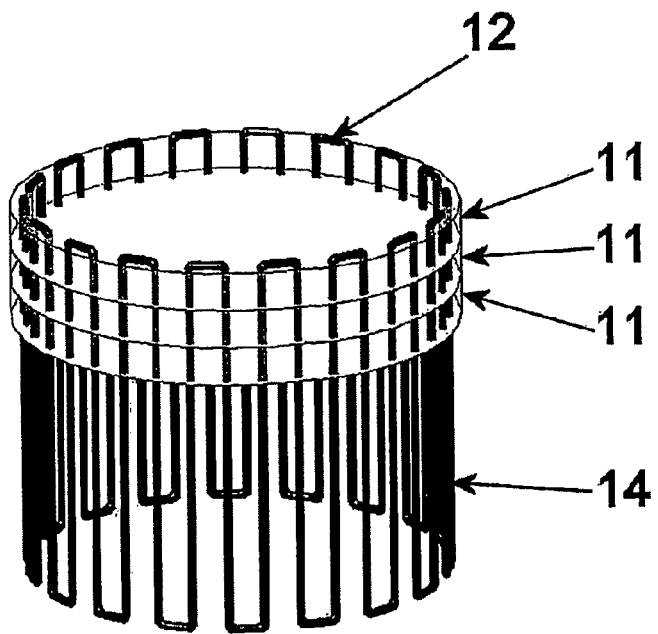
FIG. 3 is a view, similar to FIG. 1, showing a preferred development of the embodiment shown in FIG. 1.
Figure 4:
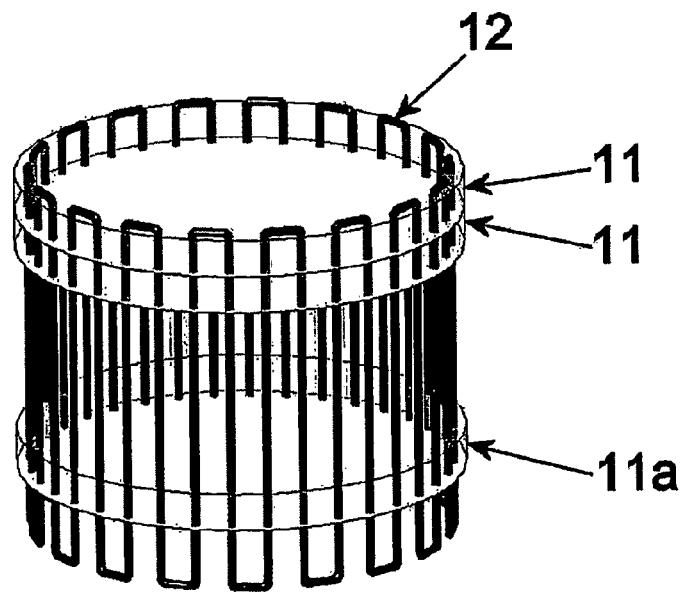
FIG. 4 illustrates mode of use of the preferred development shown in FIG. 3.

As a development of the pad 11 shown in FIGS. 1 and 2, a stacked assembly of pads 11 may be provided, as shown in FIG. 3. FIG. 4 shows an assembly of pads 11, of which a lowermost pad 11a is removable.

Referring now to FIG. 5, this is a schematic illustration of the preparation of a bone site having damaged tissue, which in the illustrated example only, is assumed to be cartilage on the bone of a joint. Adjacent portions of bone are shown by reference 20 and 21, and having overlying cartilage 22, and from which damaged cartilage tissue overlying bone section 21 has been removed. Bone section 21 therefore signifies a defective bone site, and from which a circular "plug" of damaged cartilage tissue has been removed, leaving a shallow cylindrical depression 23, extending down to the upper surface 24 of bone section 21. Subsequently or before, a groove 25 is formed about the bone site, i.e. around the periphery of the circular recess 23, then downwardly into the bone section 21 to a required depth.

Conveniently, the cylindrical recess 23, formed after extraction of damaged tissue, is circular, and similarly the groove 25 also is circular being formed by a cylindrical reamer tool. Reference 27 shows a hole drilled in the subchondral bone at the defect site, such hole being drilled to encourage bleeding and migration of bone marrow derived cells to the repair site to expedite the generation of cartilage tissue in the repair site.

Figure 5A:
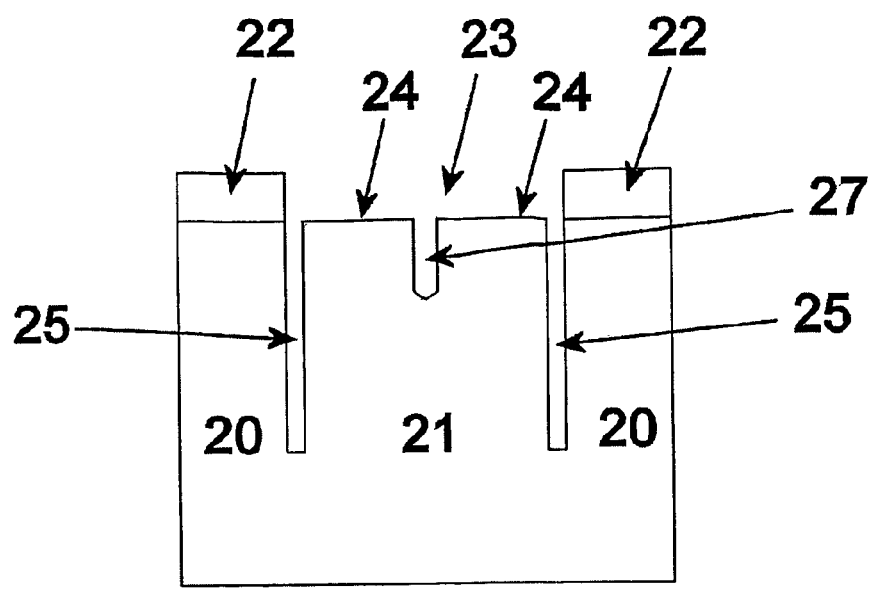
FIGS. 5a and 5b are schematic illustrations, in section and perspective respectively, of the preparation of a bone site having damaged cartilage, ready for implantation via a repair kit according to the invention.
Figure 5B:
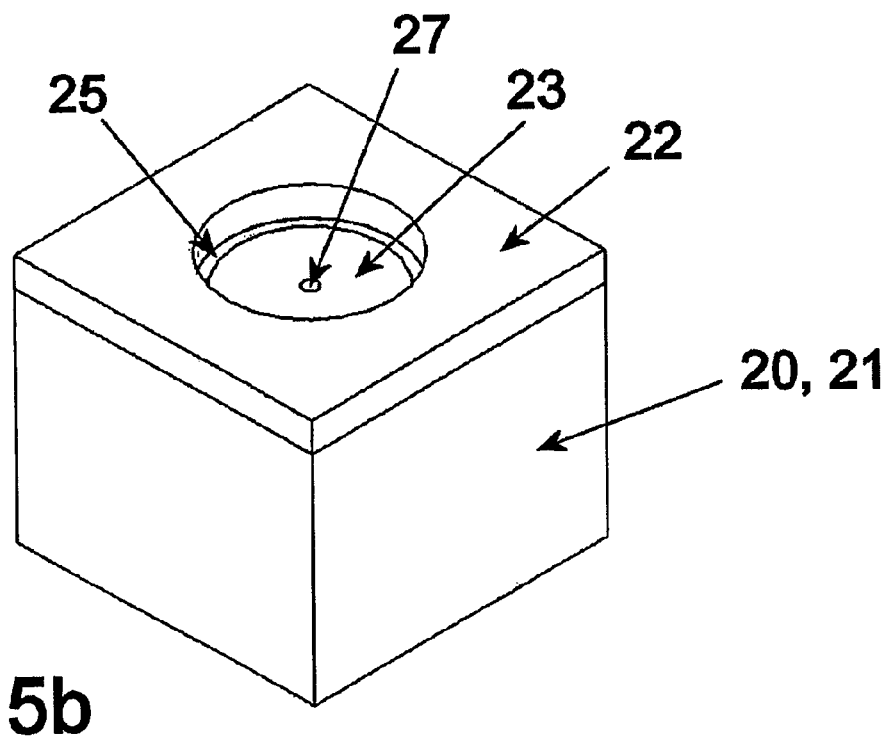
Figure 6:
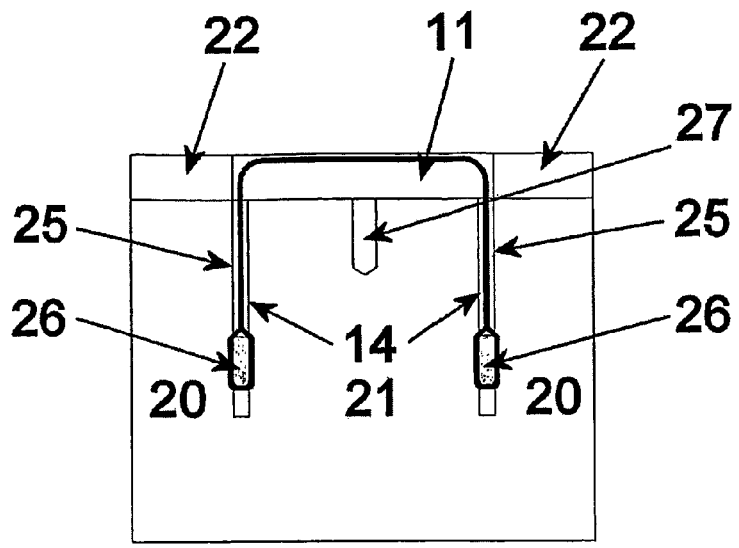
FIG. 6 is a similar illustration, and showing implantation of a repair kit on the prepared bone site.

FIG. 6 shows the implantation of a repair kit 10 on the prepared bone site of FIGS. 5a and 5b, using a retaining ring 26 (pre-assembled with the repair kit 10, or assembled just prior to implantation).

It should be understood, however, that other shapes of recess may be formed, to remove damaged tissue and similarly other shapes of groove may be formed, to surround the bone site from which damaged tissue material has been removed. A repair kit according to the invention and a method of use thereof, may be employed in such other surgical operations as described.

FIGS. 1 and 2 show the repair kit 10, constituted by pad 11 and the elongate connecting portions 14, but omits illustration of the "retaining element", examples of which will be described in more detail below.

Figure 7:
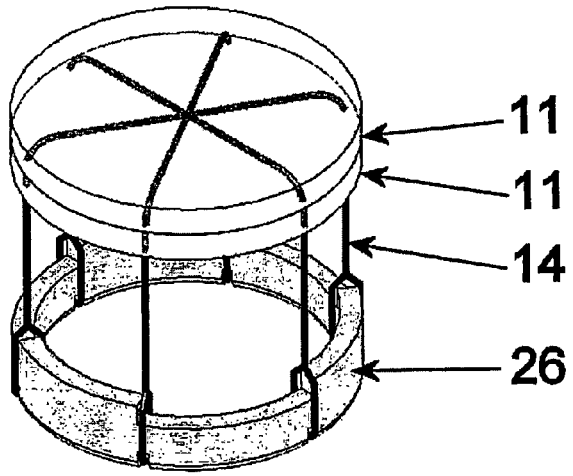
FIG. 7 is a perspective and schematic illustration of a repair kit according to the invention.

FIG. 7 shows an embodiment with a plurality of stacked pads 11, and an attached retaining ring 26 taken through the lower looped ends of the connecting portions 14. The repair kit may be pre-assembled in this form, in which case the introduction of the ring 26 to the mouth of the groove 25, followed by downward displacement of the ring 26 by a suitable tool, will pull the connecting portions 14 downwardly into the groove 25, and thereby locate and then securely place the pad or pads 11 over the defect site, i.e. overlying the exposed surface of bone section 21.

The retaining ring 26 may be rigid, and therefore preformed to the shape of the groove. Alternatively, the ring 26 may be deformable, preferably resiliently deformable, and conveniently may form a near complete circle, with slightly spaced facing ends, allowing any necessary deformation of the shape of the ring to correspond with the shape of the groove, and then allow downward displacement of the ring.

The ring 26 may be formed so as to fit into only part of the groove, in which case a further retaining portion may be provided, so that two retaining portions can act together, being introduced separately, or together, in order to apply downward pulling force to the connecting portions 14 and then anchor them in position.

FIGS. 8a, b, c, d and e shows how two separate extracted discs of damaged tissue may be removed, by drilling downwardly two separate cylindrical recesses, overlapping, followed by formation of surrounding grooves extending downwardly into the underlying bone.

Two adjacent cylindrical recesses 27 and 28 may therefore be formed, and as shown in FIGS. 8b and 8c, a cooperating pair of separate pads 29 and 30 may be provided, of which pad 30 is circular, and pad 29 is crescent shaped. Each pad 29 and 30 has elongate connecting portions 31 and 32, and corresponding partial retaining ring 33 and full or near full retaining ring 34 as shown, to pull the corresponding pad downwardly into position, and then anchor the pad in position. The pads 29 and 30 then cooperate to fill the space made available by extraction of the two cylindrical and overlapping recesses 27 and 28.

FIG. 9a illustrates schematically a repair kit having a different array of pads for the repair of a larger defect. A central circular pad 35 is surrounded by an annular or ring pad 36, and each pad has depending connecting portions 35a and 36a which are introduced into respective grooves to anchor the pads 35, 36 in required positions over the prepared bone site (FIG. 9b) from which damaged tissue has been removed.

FIGS. 10a and b show in more detail the construction of a repair kit according to the invention, and in particular the means by which elongate connecting elements, in the form of threads or sutures 37 are connected to the bio-compatible pad 38, and from which they extend away generally perpendicularly, when installed. The ends of the connecting elements 37 remote from the pad 38 are anchored to a retaining ring 39, either during factory assembly of the kit, or just prior to implantation. The retaining ring 39 has a step machined in its outer circumference, to engage a delivery tool or device to be described in detail below with reference to FIGS. 11a and b.

Figure 11:
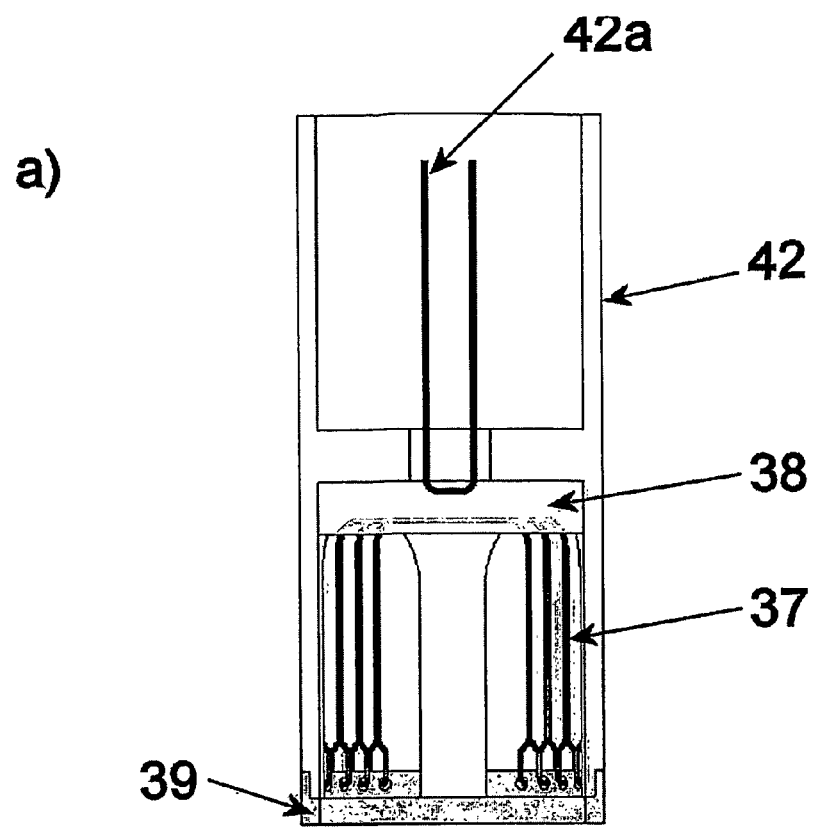
Figure 11:
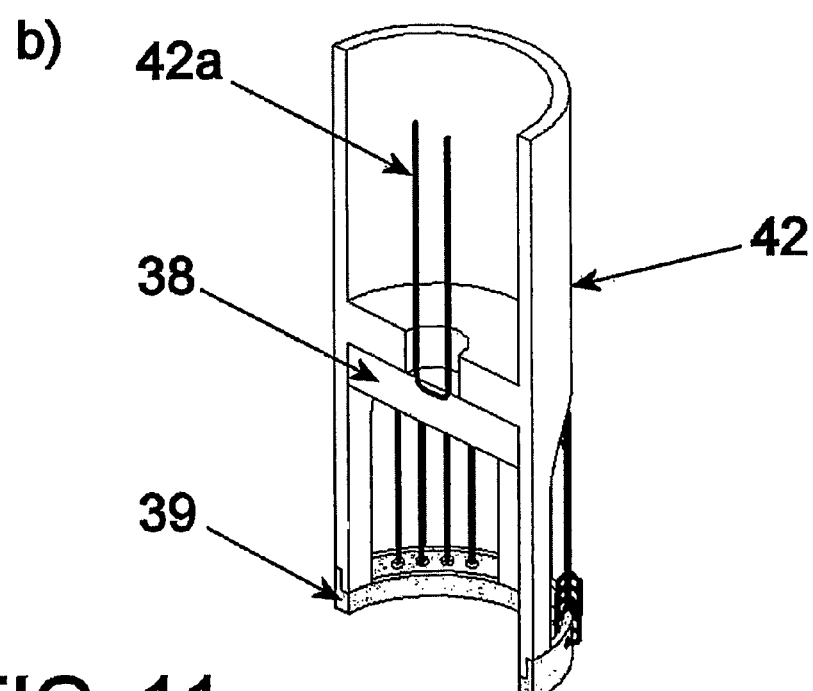

FIG. 11 shows an axial sectional view and cut-away through a delivery device 42 and the repair kit or implant device described above. The delivery device (introducer tool) as illustrated, is a one piece tool, which can be used to implant the bio-compatible pad(s) 38, which is (are) retained by threads under tension 42a, on a prepared bone site, and with the elongate connecting elements 37 and the anchor (ring) 39 being received by the groove which is formed in the bone around the prepared bone site.

The repair kit/implant device may be assembled with the tool just prior to implantation, or more preferably, they may be assembled together in a "clean room" or other mass-production area, and then supplied in sealed form ready for use by the surgeon.

FIGS. 8f, g and h show further shapes of pad which may be used in a repair kit according to the invention.

Figure 13:
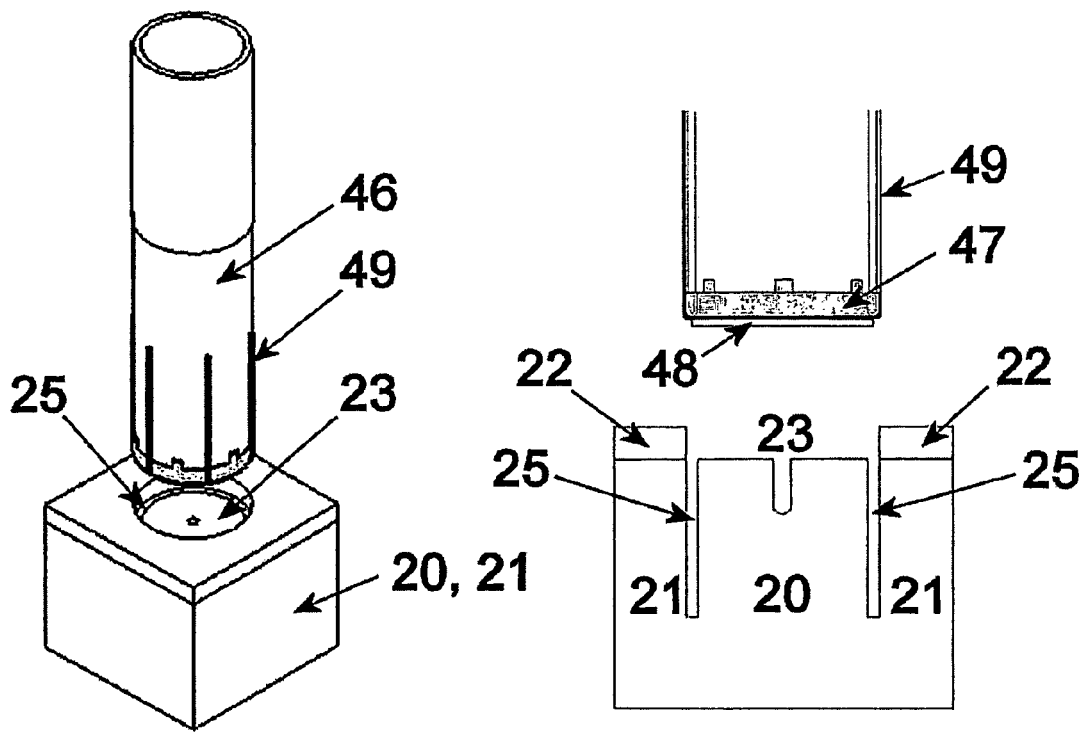
Figure 13:
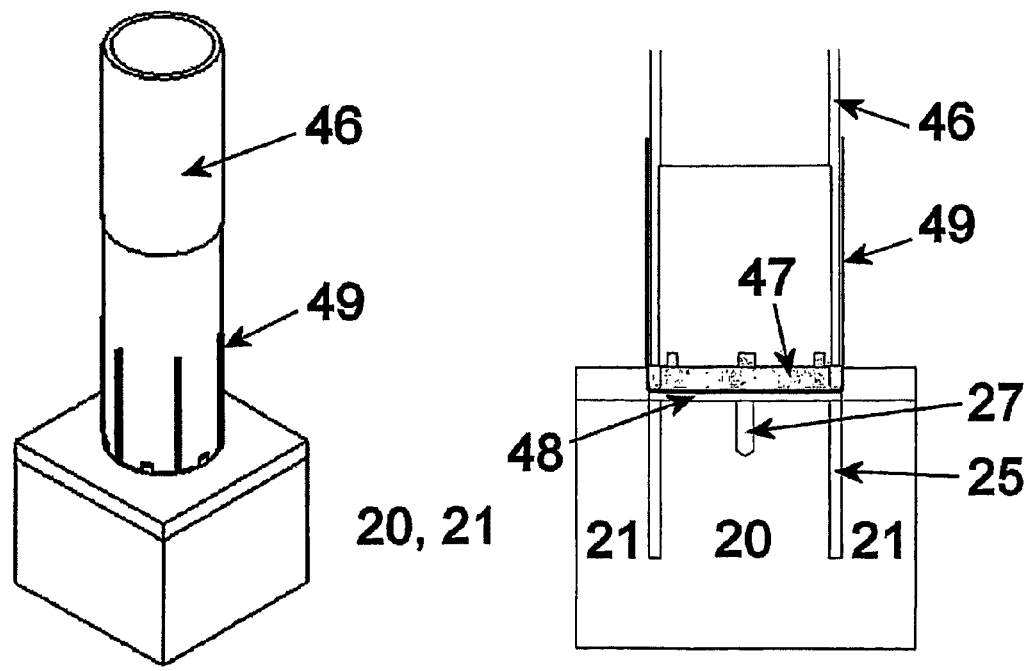

Referring now to FIGS. 12 and 13, there is shown a preferred development of the repair kit in which it is pre-assembled with a delivery device. The kit can be stored in this form ready for use, so that the delivery device acts as a holder during storage, but also operates to implant the repair components of the kit when required.

The main component of the implant is a pad 48 in the form of a scaffold through which two or more threads 49 are passed such that they protrude a certain amount beyond the edge of the scaffold. These threads are then passed over the ring 47 and are secured to the outside of an implanting or delivery device 46 by a thin membrane (such as a weak adhesive tape or film), or by a thin tubular ring made of metal, rubber or some other suitable materials (not shown). The scaffold may be disc shaped in profile so that it exactly fills the area of cartilage cleared in the implant site preparation. However, when a larger area is required, it is possible to produce scaffolds with a profile that will allow tessellation. These include a circular profile that has a point or star-shaped tooth on its periphery with a subtended angle of 120° such that three pads may be implanted in juxtaposition. Alternatively, with a subtended angle of 90°, four such pads can interfit snuggly.

Examples of pad shapes are shown in FIGS. 8f, g and h. This leads logically to another alternative where the pads are entirely hexagonal in profile, and may therefore be tessellated in indefinite numbers. These changes in profile are only slight, and may be allowed with the system disclosed as the scaffolds are deformable and may easily be retained within the implanting device 46 without fear of compromising the system.

The implanting device 46 is essentially cylindrical in form with a stepped profile at one end that locates the ring 47 of the implant in such a manner that it is held securely in place by corresponding steps on the ring. The handle of the device (not shown) also contains a bearing so that accidental rotation of the implanting device is prevented if any (unnecessary) turning movement should happen to be applied to the handle by the surgeon during the implantation procedure.

The whole system is therefore contained and implanted in one step which is described as follows:

The implanting device 46 is held perpendicularly and concentrically to the repair site and is then pushed simply down into the groove, before being retracted, leaving the implant in place. As the implanting device (46) descends into the repair site, the scaffold 48, which is held in the end of the device, locates on the top of the bone plug in the repair site, which in turn prevents the scaffold from moving. As the device 46 is pushed further, the ring 47 drags the threads 49, which are passed through the scaffold, down into the annular groove under a tension that secures the scaffold in place. Once the ring 47 reaches the bottom of the repair site, the implanting device 46 is withdrawn, leaving the ring 47, threads 49 and scaffold 48 securely located within the repair site.

The invention claimed is:

1. A method for the repair of damaged cartilage present at or on the surface of bone in an animal, including a human being, the method comprising:

forming a narrow groove around at least part of said damaged cartilage using a cutting tool, the groove extending below the damaged cartilage and into the bone;

removing the damaged cartilage within the region defined by the groove to form a cavity in the cartilage present on the surface of the bone, the narrow groove extending from the cavity into the bone;

inserting a bio-compatible replacement pad in the cavity from where the damaged cartilage has been removed, the pad configured to encourage cell in-growth at the repair site;

retaining the bio-compatible replacement pad in the cavity using an array of elongate connecting portions attached to or near the perimeter of said pad, said connecting portions extending away from the general plane of said pad at or near the perimeter of said pad in a direction towards a retaining element to provide a connection between said retaining element and said pad, each of said connecting portions connected to the retaining element and spaced apart from each other between the retaining element and the pad to allow tissue in-growth at the groove;

anchoring the bio-compatible replacement pad in said cavity by sliding said retaining element depthwise into the groove to a depth into the bone underlying said cavity to apply a downward pulling force to said connecting portions to locate and anchor said pad in said cavity;

delivering the pad, the retaining element and the connection portions to their anchored positions using an implant delivery device on which the pad, retaining element and connecting portions are preassembled;

anchoring the retaining element and pad in position by sliding the retaining element depthwise into the groove using the delivery device via a single insertion and withdrawal movement of the delivery device such that all of the retaining element is anchored in the groove at a depth of the underlying bone and is spaced apart from the pad in anchored position by a depth of the groove;

wherein the retaining element is anchored in position within the groove initially by the frictional contact between the retaining element and the side walls of the groove defined by the surrounding bone;

wherein the retaining element is slid depthwise from the region of the cavity to the underlying bone in the same orientation in which the retaining element is anchored in position at the bone relative to the pad and is preformed to have a shape corresponding generally with at least a part of the shape of the groove, from a plan view;

wherein said retaining element is spaced apart from the pad in anchored position by a length of said connecting portions located in said groove, the space between the retaining element and the pad being provided for bone ingrowth over the retaining element and the connecting portions.

2. The method according to claim 1, in which the pad is seeded with chondrocytes or cartilage-forming cells prior to implantation.

3. The method according to claim 1, in which the elongate connecting portions are formed by one or more flexible tensile elements taken or "threaded" through the pad, at or near the periphery of the pad, and which can extend generally perpendicular to the plane of the pad so as to be received by the groove with adjacent elements being spaced apart from each other to allow tissue ingrowth in the groove.

4. The method according to claim 3, in which a single filament, thread or yarn is attached to the periphery of the pad, and extends downwardly of the pad in loops of generally parallel lengths.

5. The method according to claim 4, in which the retaining element is pre-attached to the ends of the loops, so that downward movement of the retaining element into the groove pulls the loops downwardly until the pad is received by and then anchored in or at the bone site.

6. The method according to claim 1, in which the retaining element is deformable to take up the required shape, prior to introduction into the groove.

7. The method according to claim 1, in which the elongate connecting elements have looped ends and the retaining element comprises a ring, or near complete ring, which can be "threaded" through, or connected with, the looped ends of the elongate connecting elements, during the manufacture of the repair kit, or during the implantation procedures.

8. The method according to claim 1, in which the pad is circular in shape, crescent-shaped, part circular with two straight sides, hexagonal, or having other multi-sided shape such that adjacent pads can inter-fit with each other to fill the space made available during the preparation of the bone site.

9. The method according to claim 1, in which the delivery device is hollow, at least at one end thereof, and onto which the retaining element and the pad are fitted ready for presentation by the delivery device to the prepared bone site and the surrounding groove.

10. The method according to claim 9, in which the elongate connecting portions are arranged on the outer surface of the hollow end of the delivery device.

11. The method according to claim 10, in which the holding arrangement comprises a band of weak adhesive tape or the like, or a thin tubular band, for engaging the connecting portions and the outer surface of the hollow end of the delivery device.

12. The method according to claim 1, in which the elongate connecting portions are retained in position by a releasable holding arrangement.

13. The method according to claim 1, in which the delivery device is capable of being removably mounted, at its remote end, on a manually operable implant tool handle.

14. The method according to claim 13, in which the coupling between the tool handle and the delivery device includes a bearing which permits turning movement of the tool, during manipulation by the surgeon, without transfer of such movement to the delivery device.

15. The method according to claim 1, in which the cutting tool is a reaming device.

16. The method according to claim 1, in which the depth of the groove is at least five times that of the thickness of cartilage which is replaced.

* * * * *

UNITED STATES PATENT AND TRADEMARK OFFICE
CERTIFICATE OF CORRECTION

| | | |
|---|---|---|
| PATENT NO. | : 7,632,311 B2 | Page 1 of 1 |
| APPLICATION NO. | : 10/577886 | |
| DATED | : December 15, 2009 | |
| INVENTOR(S) | : Bahaa Botros Seedhom et al. | |

It is certified that error appears in the above-identified patent and that said Letters Patent is hereby corrected as shown below:

In column 7 line 48, please delete "stageds" and replace it with --stages--.

Signed and Sealed this
Third Day of May, 2011

David J. Kappos
*Director of the United States Patent and Trademark Office*